United States Patent [19]

Schiferl et al.

[11] Patent Number: 4,602,377

[45] Date of Patent: Jul. 22, 1986

[54] DIAMOND-ANVIL HIGH-PRESSURE CELL WITH IMPROVED X-RAY COLLIMATION SYSTEM

[75] Inventors: David Schiferl, Los Alamos; Barton W. Olinger, Santa Fe; Robert W. Livingston, Los Alamos, all of N. Mex.

[73] Assignee: The United States of America as represented by the United States Department of Energy, Washington, D.C.

[21] Appl. No.: 595,013

[22] Filed: Mar. 30, 1984

[51] Int. Cl.[4] .................. G21K 1/02; G01N 23/20
[52] U.S. Cl. ........................ 378/150; 378/80; 378/206
[58] Field of Search ............. 378/80, 79, 206, 147, 378/148, 150

[56] References Cited

U.S. PATENT DOCUMENTS

| 2,120,729 | 6/1938 | Chausse | 378/205 |
| 2,139,966 | 12/1938 | Loebell | 378/150 |
| 2,514,791 | 7/1950 | Parrish et al. | 378/147 |
| 2,659,017 | 11/1953 | Bartow | 378/149 |
| 2,993,993 | 7/1961 | Delong et al. | 378/150 |
| 3,160,748 | 12/1964 | Chan | 378/75 |
| 3,310,675 | 3/1967 | Prickett et al. | 378/147 |
| 3,340,396 | 9/1967 | Prickett et al. | 378/75 |
| 3,487,218 | 12/1969 | Krebs et al. | 378/153 |
| 4,200,803 | 4/1980 | Becker et al. | 378/150 |

OTHER PUBLICATIONS

Schiferl et al., "Improved X-Ray Collimation System for Diamond-Anvil High-Pressure Cells", Rev. Sci. Instrum., 54 (9), Sep. 1983, pp. 1250-1251.
Bassett et al., "X-Ray Diffraction and Optical Observations on Crystalline Solids Up to 300 Kbar", Rev. Sci. Instrum., 38 (1), Jan. 1967, pp. 37-42.

*Primary Examiner*—Carolyn E. Fields
*Attorney, Agent, or Firm*—William A. Eklund; Paul D. Gaetjens; Judson R. Hightower

[57] ABSTRACT

An adjustable X-ray collimation system for a diamond-anvil high-pressure cell of the type including a cooperable piston and cylinder and a pair of opposing diamonds located between the head of the piston and the head of the cylinder. The X-ray collimation system includes a tubular insert which contains an X-ray collimator. The insert is engageable in the bore of the piston. The collimator is mounted within the insert by means of an elastomeric O-ring at the end closest the opposed diamonds, and by means of a set of adjustable set screws at the opposite end. By adjustment of the set screws the collimator can be pivoted about the O-ring and brought into alignment with the opposed diamonds and the sample contained therein. In the preferred embodiment there is further provided a set of plugs which are insertable in the bore of the collimator. The plugs have bores of different diameters. By successively inserting plugs of progressively smaller bore diameters and adjusting the alignment of the collimator with each plug, the collimator can be quickly brought into accurate alignment with the diamonds. The collimation system allows alignment of the collimator either before or after the cell has been loaded and pressurized.

4 Claims, 5 Drawing Figures

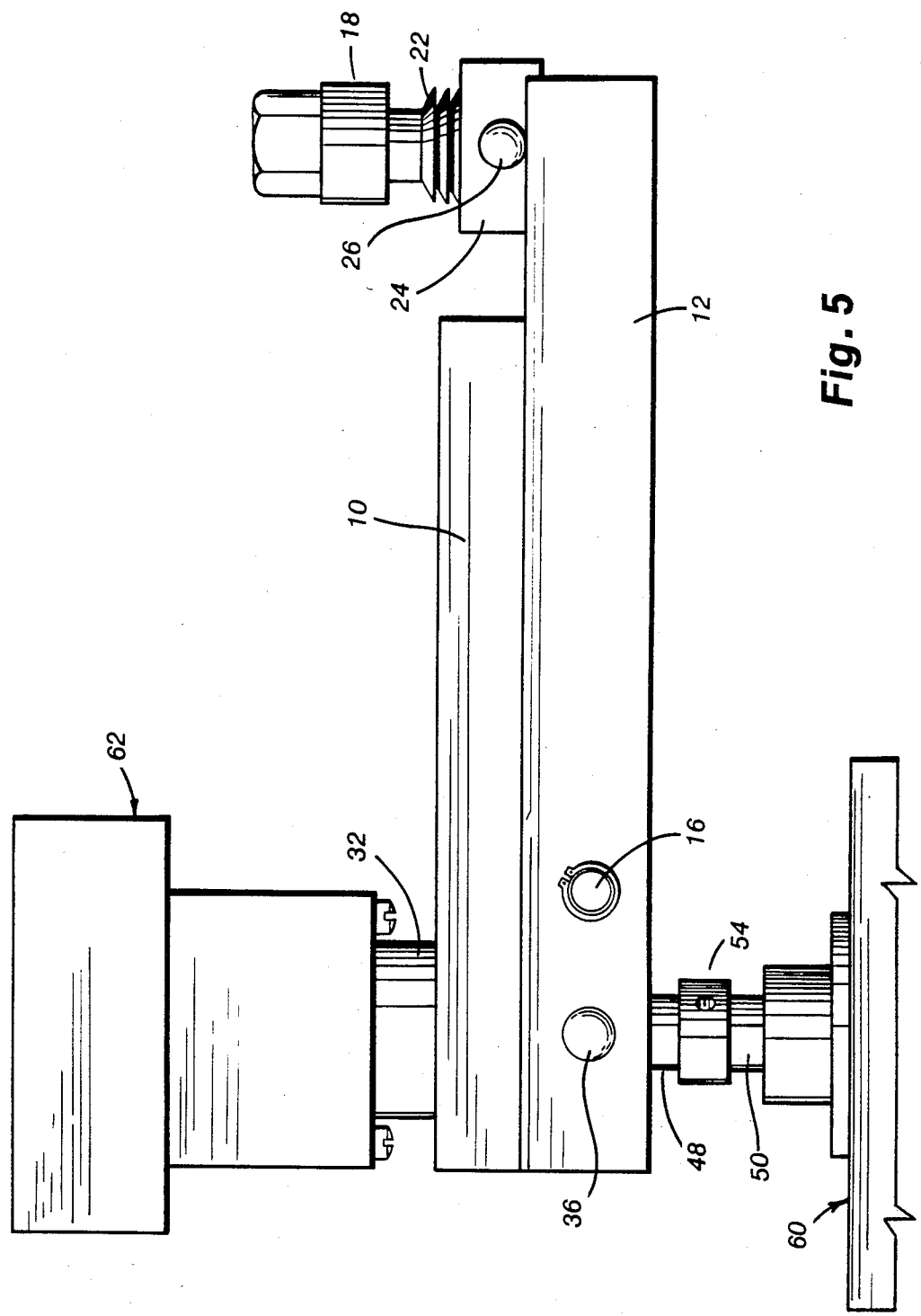

DIAMOND-ANVIL HIGH-PRESSURE CELL WITH IMPROVED X-RAY COLLIMATION SYSTEM

BACKGROUND OF THE INVENTION

The invention described herein is generally related to diamond-anvil high-pressure cells used for high pressure studies, and is also generally related to X-ray collimators such as are used in X-ray diffraction equipment and for other purposes. This invention is the result of a contract with the U.S. Department of Energy (Contract No. W-7405-ENG-36).

Diamond-anvil high-pressure cells are well-known devices which are used to study materials at high static pressures. In a typical diamond-anvil cell, two brilliant-cut diamonds, each with its culet point truncated to form a planar face, are compressed in opposition against one another. A deformable metal gasket, consisting of a flat piece of metal foil with a small hole in it, is placed between the opposing diamond faces, with the sample to be studied being contained in the hole in the foil and between the opposing diamond faces. Static pressures on the order of 600 kilobars can be readily obtained by mechanical compression of the diamonds. The primary advantage of the diamond-anvil cell is that the sample can be viewed through the two optically transparent diamonds, thus enabling spectroscopic and other optical studies to be conducted while the sample is compressed.

X-ray diffraction studies are a principal use of diamond-anvil cells. In preparation for such studies an X-ray beam must be highly collimated and directed so as to pass through the two diamonds and the sample contained between them. The X-ray beam is ordinarily collimated by means of an elongate tubular metal collimator. Such collimators have very small diameter bores in order to narrowly collimate the X-rays prior to passage through the faces of the opposed diamonds and the sample. With previously known diamond-anvil cells, the alignment of the X-ray collimator has been a difficult and time-consuming task, sometimes requiring an entire day to perform. Moreover, it has previously been impossible to remove the collimator, once it has been aligned, and replace it without having to repeat the alignment process. Nevertheless, it is sometimes necessary to remove the collimator temporarily while a sample is under pressure, in order to inspect the sample or for other purposes. Thus, in X-ray diffraction studies a great deal of time has been involved in the alignment and realignment of the X-ray collimator.

SUMMARY OF THE INVENTION

Accordingly, it is an object and purpose of the present invention to provide a diamond-anvil high-pressure cell having a readily alignable X-ray collimation system.

It is also an object and purpose to provide such an X-ray collimation system which is removable from the cell while a sample is under pressure and which can be reintroduced into the cell without need for realignment.

It is another object of the present invention to provide an X-ray collimation system which can be aligned with the diamonds of the cell prior to pressure loading of the cell and which can be introduced into the cell in an aligned state after the cell has been loaded and pressurized.

It is yet another object of the invention to provide an X-ray collimation system which can be easily and quickly aligned, either before or after pressure loading of the cell.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the present invention provides an improved X-ray collimation system in a diamond-anvil high-pressure cell. The cell includes a cylinder and a tubular piston which is slidable in the piston to effect compression of a pair of opposed diamonds located respectively on the face of the piston and the interior face of the cylinder. The X-ray collimation system comprises a threaded tubular insert which is engageable in the bore of the piston, with the insert having a first end located closest to the head of the piston and a second end which extends outside the bore of the piston, an X-ray collimator which is insertable in the bore of the tubular insert and which includes first and second ends, an elastomeric pivot means located in said insert for flexibly and pivotably retaining the collimator at the first end of the tubular insert, and adjustable locking means located at the second end of the insert for adjusting and retaining the second end of the collimator so as to be in alignment with the opposed diamonds of the high-pressure cell.

In the preferred embodiment, the elastomeric pivot means comprises an O-ring retained at the first end of the insert. The O-ring provides a flexible pivot point for the collimator, yet also reproducibly and securely retains the first end of the collimator in alignment. The locking means comprises a set of three set screws which are located at the second end of the insert, and which permit adjustment and secure retention of the second end of the collimator. Also in the preferred embodiment, the tubular insert is threaded into the bore of the piston and includes a stop face, whereby the insert can be removed from the piston while the cell is pressurized and reintroduced without impairing the alignment of the collimator.

In accordance with another aspect of the invention, there is provided a set of plugs which are insertable into the bore of the collimator and which have bores of varying diameters. During the alignment of the collimator, plugs of successively smaller bore diameter are inserted into the collimator to enable the collimator to be progressively more precisely positioned and finally locked into place when accurate alignment is attained.

These and other aspects of the invention will be more apparent upon consideration of the following detailed description of the preferred embodiment and the accompanying drawings.

BRIEF DESCRIPTION OF THE DRAWINGS

The accompanying drawings, which are incorporated in and form a part of the specification, illustrate the preferred embodiment of the present invention and, together with the description, serve to explain the principles of the invention. In the drawings:

FIG. 5 is a side view of the high-pressure cell as it is installed in combination with an X-ray source and an X-ray diffraction camera.

DETAILED DESCRIPTION OF THE PREFERRED EMBODIMENT

Figure 1:
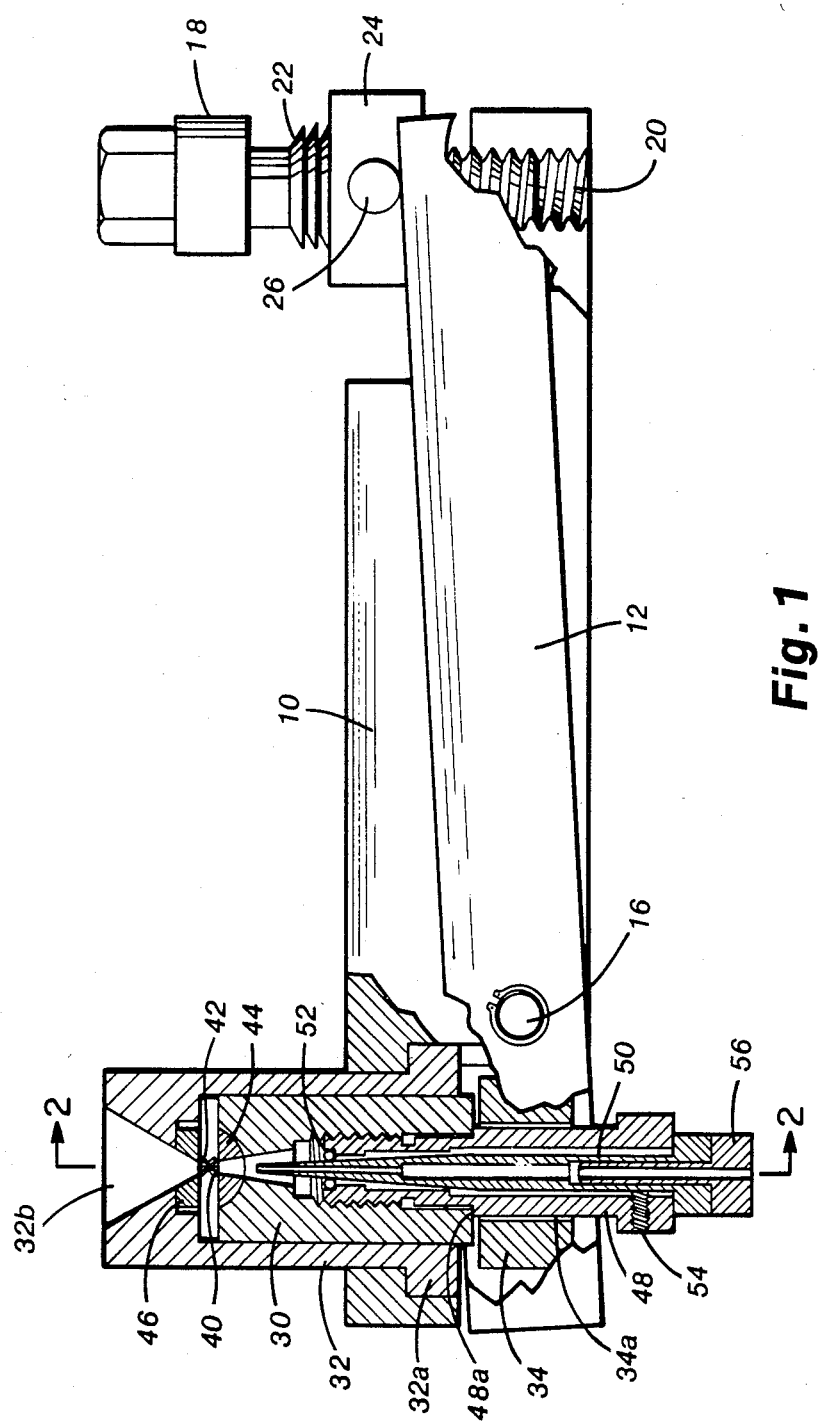
FIG. 1 is a side view in partial cross section of a diamond-anvil high-pressure cell equipped with the X-ray collimation apparatus of the present invention.
Figure 2:
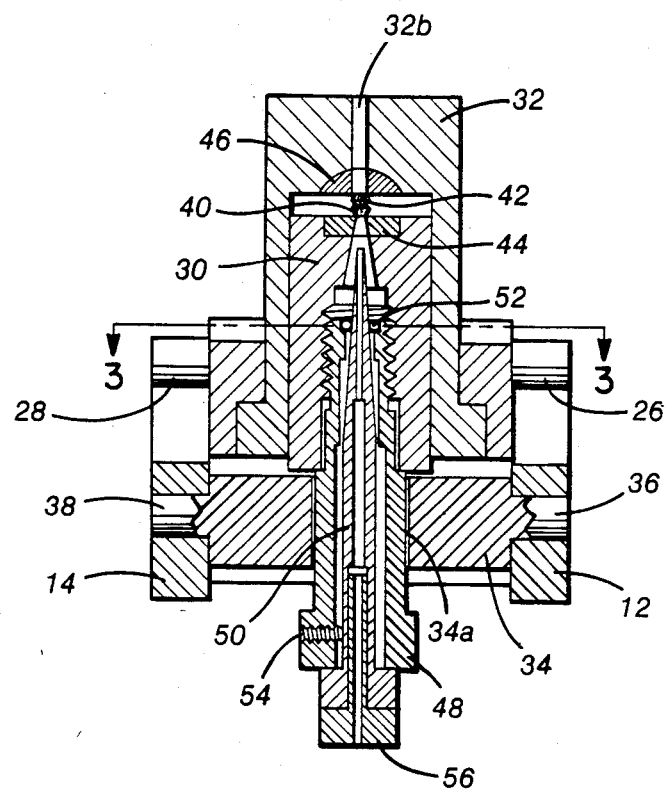
FIG. 2 is an end view in cross section of the high-pressure cell of FIG. 1, taken along section line 2—2 of FIG. 1.
Figure 3:
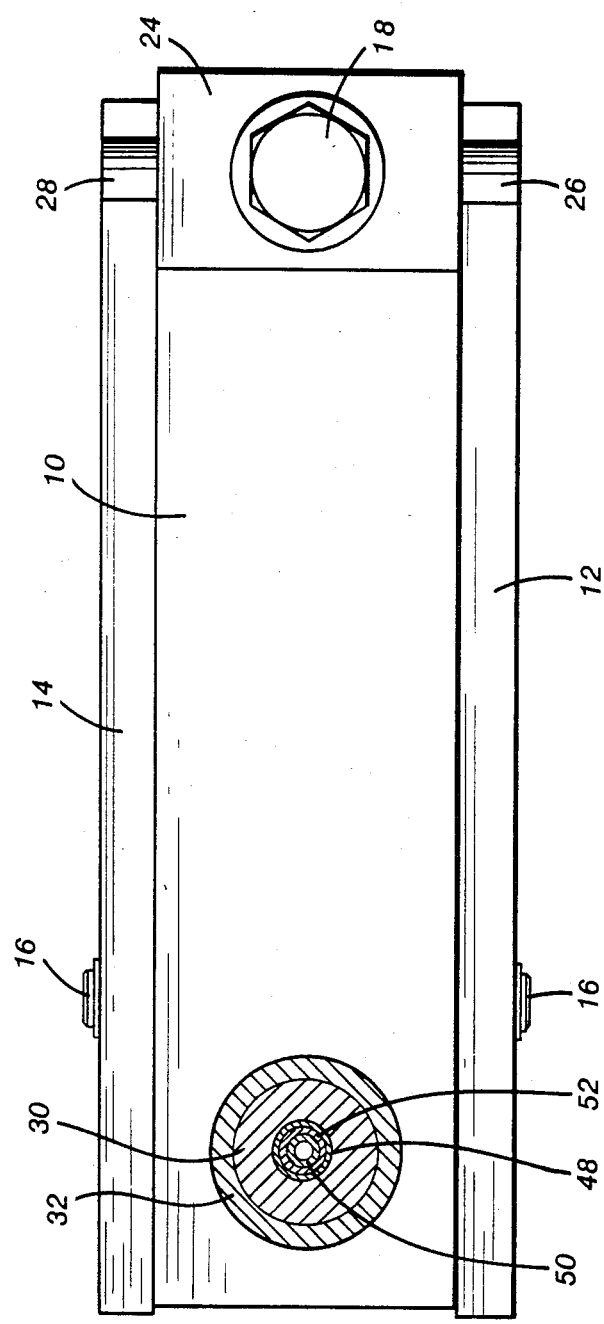
FIG. 3 is a plan view in partial cross section of the high-pressure cell of FIG. 1, taken along section line 3—3 of FIG. 2.
Figure 4:
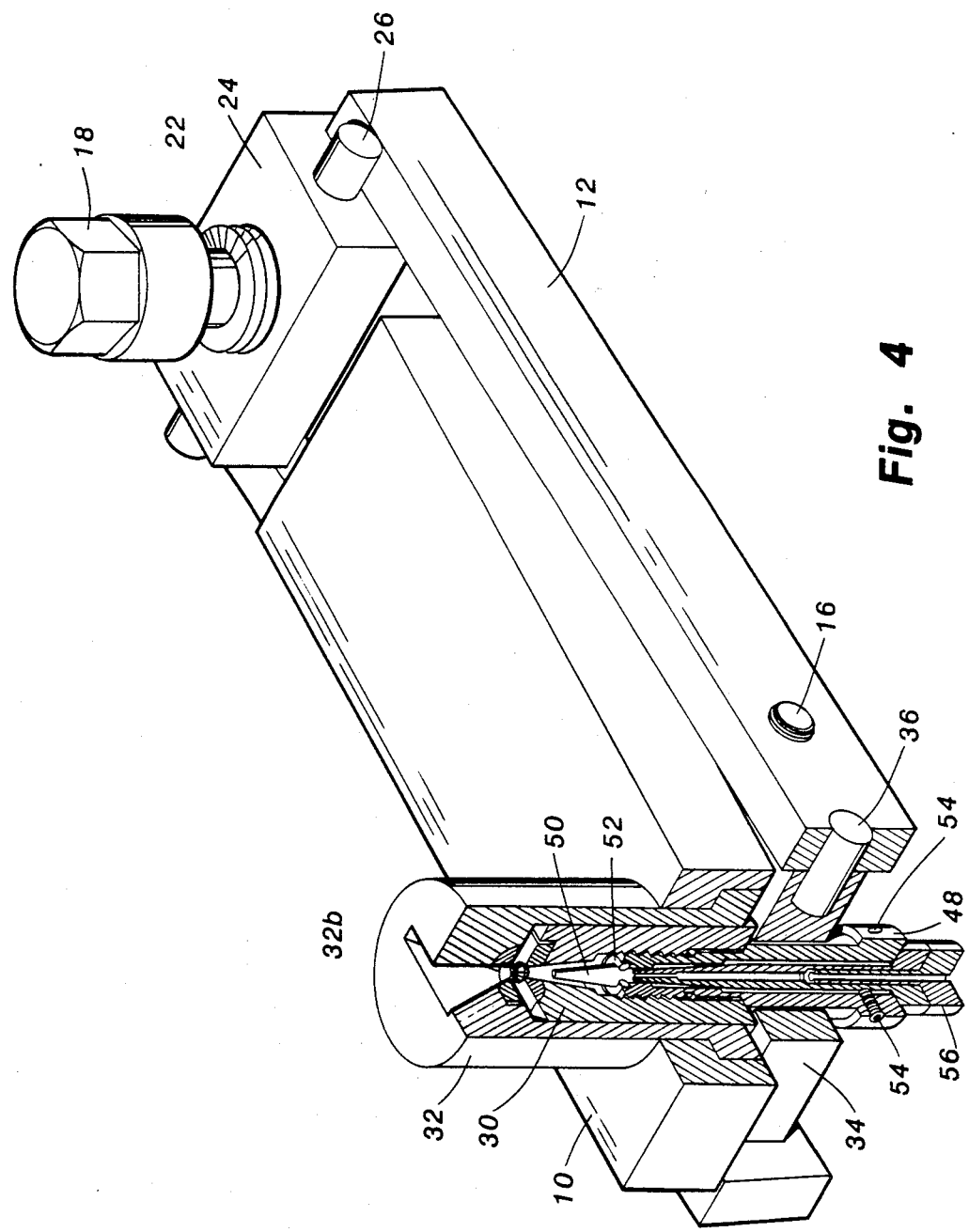
FIG. 4 is an isometric view in partial cross section of the high-pressure cell illustrated in FIGS. 1 through 3.

Referring to FIGS. 1 through 3, there is illustrated a diamond-anvil cell equipped with the X-ray collimation system of the present invention. The cell includes a central lever arm body 10 and a pair of side arms 12 and 14. The side arms swing in unison with respect to the central body 10 about a pivot pin 16 which passes through the central body 10. Swinging of the side arms 12 and 14 is effected by means of bolt 18 which is engaged in a threaded bore 20 in the central body 10. The shaft of the bolt 18 passes through a set of three Belleville spring washers 22 and through a hole in a rectangular collar 24, such that the head of the bolt and the washers 22 drive the collar 24 downwardly when the bolt 18 is screwed into the threaded bore 20. The collar 24 includes integral cylindrical pivot pins 26 and 28 which extend from the opposite ends of the collar and rest on the upper surfaces of the lever arms 12 and 14 respectively.

The diamond-anvil cell further includes a piston 30 and an associated cylinder 32. The cylinder 32 is fitted in a hole in the central body 10. Upward motion of the cylinder is prevented by an integral flange 32a at the base of the cylinder, which resides in a conformably shaped annular recess centered around the hole in the body 10.

The piston 30 is free to slide up and down within the cylinder 32. The piston is driven in this respect by a rectangular thrust block 34 which is pivotably attached to the two lever arms 12 and 14 by integral cylindrical pivot pins 36 and 38, respectively. The thrust block 34 includes a central bore 34a to accommodate the X-ray collimator, described further below. When the bolt 18 is tightened down, the lever arms 12 and 14 pivot about pivot pin 16, thereby driving the thrust block 34 upwardly against the base of the piston, and thereby driving the piston 30 upwardly in the cylinder 32. The thrust block 34 is pivotably attached to the lever arms to ensure that the upward force is applied to the piston evenly and in the direction of the axis of the piston/cylinder combination.

A first diamond 40 is mounted on the top of the piston. A second diamond 42 is attached to the underside of the upper closed end of the cylinder. Each diamond is brilliant-cut, that is, cut in the shape commonly used in diamond rings, however with the pointed tip truncated so as to form a flat face. It is the faces formed by truncating the culet tips of the diamonds that are opposed to one another; the larger planar faces, which are the outer faces in a typical diamond ring, face the piston and cylinder so as to receive the compressive forces applied therefrom.

The diamonds 40 and 42 rest against semi-cylindrical tungsten carbide rockers 44 and 46, respectively. The rockers are set into semi-cylindrical recesses formed in the upper surface of the piston and the lower surface of the cylinder, respectively. The rockers are oriented with their cylindrical axes at right angles to one another. The rockers provide a gimbal-like support for the diamonds, ensuring that the opposing faces of the two diamonds are engaged and compressed only in a parallel alignment. This is important because, at the high pressures involved, any misalignment or nonparallel engagement of the diamonds can quite easily result in fracturing of one or both of the diamonds.

Each rocker includes a vertical bore through which light or X-rays may be passed. The bores in the rockers are sized relative to the diamonds such that the large planar faces of the diamonds can be centered over the bores and receive the force applied through the rockers to the diamonds.

The upper end of the cylinder 32 includes a slot 32b which tapers to an aperture centered on the bore of the associated rocker 46. The piston 30 includes a central bore, described further below, which tapers down to an aperture centered on the piston rocker 44. With this arrangement light or X-rays can be directed through the piston and cylinder assembly, passing only through the two diamonds and the sample contained between them.

A small deformable metal gasket is ordinarily positioned between the two diamonds, but is not shown in the figures because of its small size. The gasket consists of a piece of metal foil with a small hole which is centered between the faces of the diamonds. A liquid or solid sample is placed in the hole in the foil and compressed between the diamonds. Occasionally the foil will deform under pressure and the hole will wander or change shape, thus necessitating realignment of the light beam or X-ray beam that is directed through the sample.

The diamond-anvil cell as thus far described is known in the prior art and forms no part of the present invention. The present invention lies in the X-ray collimation apparatus described below. In this regard, the central bore of the piston 30 is threaded to receive a threaded tubular brass insert 48. The insert 48 passes through the bore 34a in the thrust block 34 and is threaded into the piston 30. A shoulder 48a on the shaft of the insert 48 abuts against the base of the piston 30, whereby the insert 48 can be removed from the piston and reinserted in a precisely reproducible position.

A tubular X-ray collimator 50 extends through the central bore of the tubular insert 48. The collimator is formed of stainless steel and includes a lead tip (not distinguished in the figures) with a bore drilled through it. The collimator generally tapers upwardly to the lead tip. The bore in the collimator is typically 100 to 240 micrometers in diameter.

The upper end of the collimator is held in position in the insert 48 by means of an elastomeric O-ring 52. The lower end of the collimator 50 is secured by a set of three set screws 54 which pass radially through the lower end of the insert 48. The O-ring 52 is set into an annular recess formed around the opening of the bore at the upper end of the insert 48. The O-ring provides a flexible pivot point about which the collimator may be pivoted, yet also retains the collimator securely in place once the desired orientation is attained. The set screws 54 are located at the lower end of the insert where they may be adjusted while the insert and the collimator are installed in the piston and a sample is under pressure.

A removable plug 56 is inserted into the bore of the collimator. The plug 56 is one member of a set of plugs which are insertable in the bore of the collimator and which have internal bores of different diameters. In the preferred embodiment the set consists of seven plugs having bore diameters of 150, 180, 210, 240, 300, 800 and 1,600 microns, respectively. The various plugs are interchangeable and facilitate the procedure used to align the collimator.

The collimator system may be aligned either before or after a sample has been loaded into the cell and pressure applied. To align the collimator prior to loading, the collimator 50 and insert 48 are positioned over a small light source, for example a 3 mm hole in a small table under which a light is located. With the collimator pointed upwardly, a 60× microscope is focused on the tip of the collimator and the collimator is positioned so that the light shining upwardly through the hole in the table is visible through the tip of the collimator with the microscope. The insert 48 is then threaded into the piston 30 until it is firmly seated. With the set screws 54 loosened and the piston/insert/collimator assembly positioned over the light source, the piston and insert are then rocked over the collimator until light is observed passing through the diamond 40 at the top of the piston. The set screws 54 are then gradually tightened, keeping the piston and insert positioned so that the light passes through the diamond 40. The set screws are finally adjusted so that the light passes directly through the center of the diamond culet tip face. This procedure takes approximately ten minutes. Prior to the development of the present invention, alignment of similar X-ray collimators took as much as a day.

If the cell is already loaded with a transparent sample under pressure, an alternative procedure may be used whereby the sample need not be depressurized. This may be necessary if, for example, the hole in the gasket between the diamonds has deformed or wandered. The alternative procedure is similar to the procedure described above. However, the loaded cell is too cumbersome to be rocked about the collimator in the same manner as the piston alone can be. Hence, the cell is mounted firmly upside down in such a way that the collimator can be pivoted about the O-ring 52. The plug 56 with the largest bore (1.6 mm) is inserted in the collimator, and the collimator is rocked until light is observed passing through the diamonds and the sample contained between them. The set screws are then advanced, but not tightened, so as to limit the range of motion of the collimator in the insert 48 to that range through which light can be seen passing through the diamonds. Plugs with successively smaller bores are then inserted into the collimator, with the set screws being advanced in the same way each time, until the light passing through the collimator is centered on the sample between the two diamonds, whereupon the set screws are finally tightened to lock the collimator in alignment with the sample.

Once the cell is loaded and the collimator is aligned, the cell is positioned to receive X-rays from an X-ray source, and a camera or other suitable detector is positioned to receive the X-rays passing through the collimator, the diamonds and the compressed sample. FIG. 5 illustrates the high-pressure cell positioned between an X-ray source 60 and X-ray camera 62. The removable plugs 56 may be successively inserted, in much the same manner described above, in order to align the collimator 50 with the beam of X-rays from the source 60.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. In a diamond-anvil high-pressure cell having a tubular piston and a cylinder in which the piston is slidable to effect compression of a pair of opposed diamonds located between said piston and said cylinder, said piston including a central bore opening on one end, an adjustable X-ray collimation system comprising a tubular insert engageable in said bore of said piston, said insert including a central bore and having first and second ends, with said first end of said insert being closest to the said opposed diamonds and said second end of said insert extending out of the open end of said piston, a collimator insertable in said bore of said tubular insert, said collimator having a central bore and having first and second ends corresponding respectively with said first and second ends of said insert, elastomeric pivot means mounted in said bore of said insert at said first end of said insert for flexibly retaining said first end of said collimator while allowing said collimator to pivot within said pivot means, and adjustable locking means located at said second end of said insert for adjusting and securing said second end of said collimator so as to be in alignment with said opposed diamonds.

2. The X-ray collimation system defined in claim 1 wherein said adjustable locking means comprises a set of three radially oriented set screws passing said insert and operable to secure said second end of said collimator.

3. The X-ray collimation system defined in claim 1 wherein said elastomeric pivot means comprises an O-ring set into an annular recess in said first end of said tubular insert, and wherein said first end of said collimator is cylindrically tapered so as to fit cooperably in said O-ring.

4. The X-ray collimation system defined in claim 1 wherein said tubular insert and said bore of said piston are each threaded so as to be engageable with one another, and wherein said insert includes an external shoulder which abuts against said open end of said piston, whereby said insert and said collimator secured therein can be removed from said piston and subsequently replaced in an accurately reproducible position without necessitating realignment of said collimator.

* * * * *